United States Patent
Knebelman et al.

(10) Patent No.: US 6,634,353 B1
(45) Date of Patent: Oct. 21, 2003

(54) METHODS OF TREATING RESPIRATORY DISORDERS

(76) Inventors: Stanley Knebelman, 1445 City Line Ave., Wynnewood, PA (US) 19096; Alan G. Deeley, 226 W. Boardman St., Youngstown, OH (US) 44503

( * ) Notice: Subject to any disclaimer, the term of this patent is extended or adjusted under 35 U.S.C. 154(b) by 0 days.

(21) Appl. No.: 09/528,013

(22) Filed: Mar. 17, 2000

Related U.S. Application Data

(60) Provisional application No. 60/124,937, filed on Mar. 18, 1999.

(51) Int. Cl.$^7$ .............................................. A61C 19/04
(52) U.S. Cl. .................................... 128/200.24; 433/72
(58) Field of Search .............................. 433/72, 68, 69, 433/6, 24; 33/513, 514; 128/848, 859, 206.29, 207.15, DIG. 26, 200.26, 200.24

(56) References Cited

U.S. PATENT DOCUMENTS

| | | | | |
|---|---|---|---|---|
| 4,382,783 A | * | 5/1983 | Rosenberg | 433/19 |
| 5,028,232 A | * | 7/1991 | Snow | 433/24 |
| 5,092,346 A | * | 3/1992 | Hays et al. | 128/848 |
| 5,409,017 A | * | 4/1995 | Lowe | 128/848 |
| 5,683,244 A | * | 11/1997 | Truax | 433/6 |
| 5,692,521 A | * | 12/1997 | Leasure-Nelson | 128/848 |
| 5,755,219 A | * | 5/1998 | Thornton | 128/201.18 |
| 5,794,627 A | * | 8/1998 | Frantz et al. | 128/848 |
| 5,829,441 A | * | 11/1998 | Kidd et al. | 128/848 |
| 5,848,891 A | * | 12/1998 | Eckhart et al. | 433/9 |
| 5,868,138 A | * | 2/1999 | Halstrom | 128/848 |
| 5,885,073 A | * | 3/1999 | Kussick | 433/6 |
| 5,947,724 A | * | 9/1999 | Frantz et al. | 433/19 |
| 5,954,048 A | * | 9/1999 | Thornton | 128/201.18 |
| 5,957,133 A | * | 9/1999 | Hart | 128/207.14 |
| 5,983,892 A | * | 11/1999 | Thornton | 128/201.26 |
| 6,041,784 A | * | 3/2000 | Halstrom | 128/848 |
| 6,092,523 A | * | 7/2000 | Belfer | 128/848 |
| 6,099,304 A | * | 8/2000 | Carter | 433/19 |
| 6,109,265 A | * | 8/2000 | Frantz et al. | 128/848 |
| 6,155,262 A | * | 12/2000 | Thornton et al. | 128/859 |
| 6,161,542 A | * | 12/2000 | Halstrom | 128/848 |
| 6,209,542 B1 | * | 4/2001 | Thornton | 128/206.29 |
| 6,273,859 B1 | * | 8/2001 | Remmers et al. | 600/529 |
| 6,305,376 B1 | * | 10/2001 | Thornton | 128/848 |

OTHER PUBLICATIONS

"Treatment of Sleep Apnea", AADMS, vol. 14, Issue 1, p. 5.
"Craniometrics Technique Guide", Dental Equipment & Supplies, Sep./Oct. 1998, by Knebelman.

* cited by examiner

*Primary Examiner*—Aaron J. Lewis
*Assistant Examiner*—Mital Patel
(74) *Attorney, Agent, or Firm*—Dann, Dorfman, Herrell and Skillman; Henry H. Skillman

(57) ABSTRACT

A method of treating a patient having a malocclusion between the upper and lower mandibles, and obtaining optimum relative positioning of the mandibles. The treatment is useful in correcting respiratory conditions such as sleep apnea, and in prosthodontics and implantology. The method comprises measuring the malocclusion and determining the variation of the malocclusion from an optimal line occlusal contact, then mounting a dental appliance on one or both of the upper and lower mandibles and providing points of engagement on the exposed surface of the appliance to engage the other mandible as it is moved towards the closed position against the one mandible, to thereby reposition the mandibles in a direction toward line occlusion. After one or more periods of use of the appliance, the appliance is modified until the mandibles achieve line occlusion. To reinforce the treatment, at times of repose, the patient's mandibles may be biased toward closure so as to effect relative displacement of the mandibles from the maloccluded positioning toward the nine positioning.

8 Claims, 1 Drawing Sheet

METHODS OF TREATING RESPIRATORY DISORDERS

This applications claims priority of U.S. Provisional Patent Application No. 60/124,937, filed Mar. 18, 1999.

FIELD OF THE INVENTION

The present invention relates to the treatment of respiratory disorders and has particular application to effecting a physiological change in the patient to correct the cause of the respiratory disorder.

BACKGROUND OF THE INVENTION

Respiratory disorders occur in patients, resulting in a variety of effects such as sleep apnea, snoring, labored breathing, oxygen starvation, and the resulting physical impairments arising from such disorders.

Severe cases of breathing impairment are treated by oxygen therapy. Snoring is treated by various techniques for causing the patient to assume a sleeping position or orientation which avoids or reduces the likelihood of obstruction of the airway which may be the cause of the snoring. Snoring often accompanies an apnea condition in which the patient has repeated episodes of interrupted breathing during sleep. Such interruptions are normally caused by temporary blockage of the airway, for example by reason of lack of muscle tone in the tissue surrounding the airway which allows the tissue to block the airway. Surgical treatment of apnea involves the excision of the tissue causing the blockage and frequently the surgery treatment fails to correct the problem. A more common treatment is the use of continuous positive airway pressure (CPAP). In this treatment, the patient wears a nasal mask which provides a positive airway pressure in the nostrils which splits the airway open and prevents tissue from occluding it. Prescribing the proper level of positive air pressure is accomplished in a sleep laboratory by trial-and-error.

Snore guards in the form of dental appliances have been effective for some patients to reduce snoring and concomitantly reduce the incidence of apnea. Snore guards normally maintain the oral cavity in a position which ameliorates the snoring.

The prior treatments for respiratory disorders have involved treatment of the symptoms rather than treatment of the cause.

SUMMARY OF THE PRESENT INVENTION

The present invention provides a method for diagnosing and treating the cause of respiratory disorders, and is also useful in prosthodontics and implantology to assure optimum relative positioning of the mandibles.

The present invention provides a method for determining the deviation of the lower mandible from the optimum relationship with the upper mandible. The optimum position of the lower mandible provides a maximum contact between the teeth when the posterior teeth fit tightly together. For patients whose mandibles have a malocclusion or deviation from the optimum position, the muscles of the face effect an adapted position of the jaw to accommodate the malocclusion causing a perpetuation of the malocclusion.

The present invention provides a treatment for respiratory disorder in which the occlusion of the mandibles is determined and a corrective therapy is employed to effect optimum positioning of the mandibles and correction of the adaptive positioning of the jaw.

BRIEF DESCRIPTION OF THE DRAWINGS

The invention will be described more fully hereinafter in connection with the accompanying drawings, wherein.

DESCRIPTION OF THE PREFERRED EMBODIMENTS

Figure 1A:
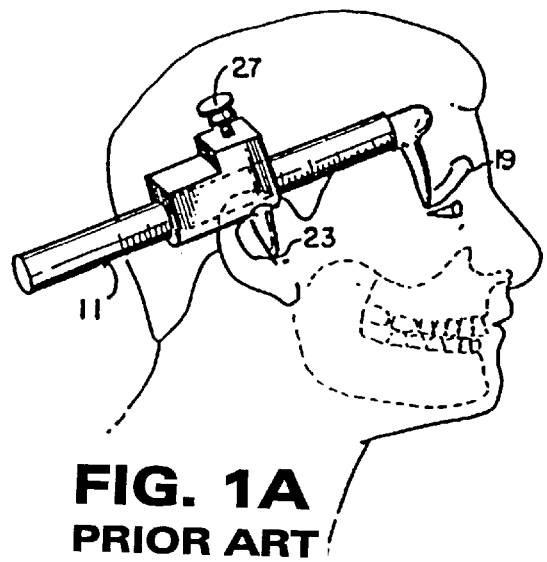
FIGS. 1A and 1B illustrate a device useful in performing the method of the present invention.
Figure 1B:
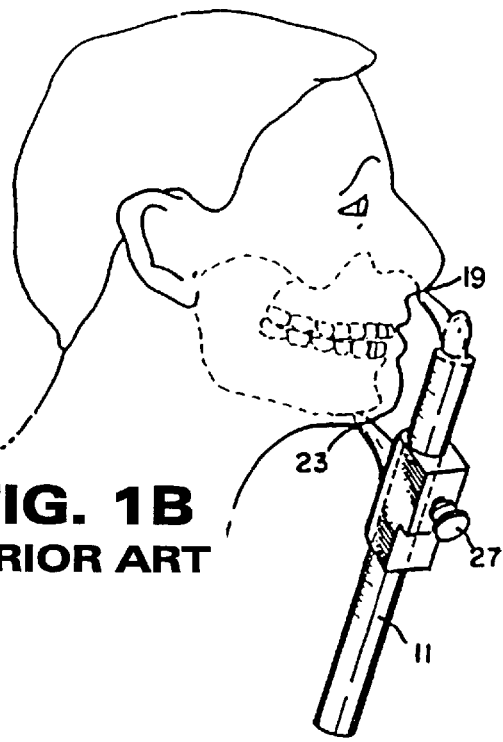

In performing the treatment according to the present invention, a patient having a habitual malocclusion of the jaws was treated to correct the adapted positioning of the jaws so as to provide an optimal positioning. In the optimal position, with the posterior teeth fitting tightly together, there is maximum contact throughout the arch when the hinge joint of the jaws effects jaw closure. The measuring device 11 of FIGS. 1A and 1B includes tip portions 19 and 23 which are adjustable relative to each other and may be anchored at an adjusted. position by a set screw 27. The adjusted position is recorded on an index along the shaft of the device 11. As described in U.S. Pat. No. 4,718,850, the device is used to accurately determine the vertical dimension of occlusion in a scientific manner which is not dependent upon the skill or art of the dental technician.

Figure 2:
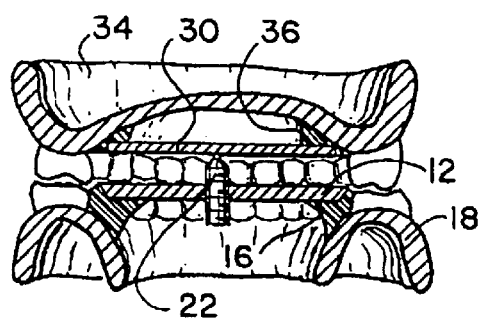
FIG. 2 is a sectional view showing a second device useful in performing the present invention.

The centering position of the occlusion is measured and determined by a device as shown in FIG. 2 and as described in U.S. Pat. No. 3,068,570. In this device, there is a base plate 12 and an upper plate 30 with a central bearing screw 22. The upper disc 30 receives and establishes the center position of the plate when it is anchored between the upper mandible 34 and the lower mandible 18, for example by dental wax as indicated at 36, and the lower plate is anchored by the dental wax 16.

These devices may be used to determine the variation of the normal positioning of the mandibles, i.e. the malocclusion, prior to treatment and are used during treatment to measure the correction achieved by the treatment.

The treatment of the patient is obtained by the use of a dental appliance consisting in the present instance of tooth guard which fits over the teeth in one mandible and has points of engagement on the exposed area of the guard to receive the teeth of the other mandible and to reposition the mandibles toward the desired occlusion, i.e. the optimal line occlusal contact, with the teeth fitting tightly together throughout the entire maximum contact.

Preferably, over the course of treatment, the use of the appliance corrects the muscular adapted positioning of the jaw so as to cause the jaw to return to maximum contact so as to reestablish the occlusion to an optimal line occlusal contact. At this point, a permanent appliance is made to be used during periods of repose to maintain the mandible in optimal line occlusal contact.

Prior to retiring, the patient substitutes an appliance having rubber bands or other biasing means which, at times of repose, will cause the jaw to close on the appliance and reposition the other mandible so as to condition the muscles to assume optimal line contact.

For severe malocclusions, it may be necessary to provide appliances for both the upper and the lower jaw which then cooperate with each other rather than having a single appliance which cooperates with the opposing teeth. Over the course of treatment, the appliances are modified or adjusted to accommodate the repositioning which has occurred by reason of the course of treatment so that by the end of the course of treatment, the malocclusion is corrected. This modification may be achieved by using a series of appliances or by using an adjustable dental appliance to reposition the mandibles toward optimal line occlusal contact, maintaining the appliance for a treatment period, then replacing or adjusting the appliance to reposition the mandibles further in a direction toward the optimal line occlusal contact for a further treatment period, and repeating the procedure until it achieves the optimal line occlusal contact. As the occlusion is corrected, the daytime appliances may be used less frequently and at the end of the treatment, it anticipated that the nighttime appliance may be used sparingly. After the treatment for the malocclusion, the patient may be subjected to prosthodontics or implantology.

We claim:

1. A method of treating apnea in a patient having sleep apnea and a malocclusion between the upper and lower mandibles comprising the steps of:

measuring and determining a centering position of the malocclusion in the patient having sleep apnea, and determining a variation of the malocclusion from an optimal line occlusal contact when in the centering position; and mounting a dental appliance on one of the upper and lower mandibles of the patient and providing points of engagement on an exposed surface of the appliance to engage the other upper mandible as it is moved towards a closed position relative to said one mandible and to reposition the other mandible in an adjusted position in a direction toward said optimal line occlusal contact.

2. A method according to claim 1 wherein including the further step of providing means to bias the mandibles towards the closed position at times of repose of the patient so as to effect relative displacement of the mandibles from the maloccluded positioning toward said adjusted position.

3. A method according to claim 1 including the step of maintaining the appliance on the one mandible for a at least a first treatment period;

thereafter removing the appliance and measuring and determining the centering position of the malocclusion; and determining the variation of the malocclusion from an optimal line occlusal contact;

mounting a second dental appliance on one of the upper and lower mandibles and providing points of engagement on the exposed surface of the appliance to engage the other upper mandible as it is moved towards the closed position relative to said one mandible and to reposition the other mandible in a direction toward said optimal line occlusal contact;

maintaining the second appliance on the one mandible for a at least a next treatment period; and repeatably mounting additional appliances after additional treatment periods until the variation measured after removing the appliance is reduced to a minimum and the mandibles are in a desired position of optimal occlusal line contact.

4. A method according to claim 3 wherein including the further step of providing means to bias the mandibles towards the closed position at times of repose of the patient so as to effect relative displacement of the mandibles from the maloccluded positioning toward said adjusted position.

5. A method of treating a patient having sleep apnea and a malocclusion between the upper and lower mandibles comprising the steps of:

measuring and determining a centering position of the malocclusion in the patient having sleep apnea and determining a variation of the malocclusion from an optimal line occlusal contact when in the centering position;

mounting an adjustable dental appliance on one of the upper and lower mandibles and providing points of engagement on an exposed surface of the appliance to engage the other mandible as it is moved towards a closed position relative to said one mandible and to reposition the other mandible in an adjusted position in a direction toward said optimal line occlusal contact;

maintaining the appliance on the one mandible for a at least a first treatment period;

after the first treatment period adjusting the appliance so that it engages said other mandible to reposition the other mandible further in a direction toward line occlusion, and maintaining the appliance for a further treatment period;

repeating said adjusting of the appliance until it achieves repositioning of said other mandible into line occlusion with the one mandible.

6. A method of treating a patient having a malocclusion between the upper and lower mandibles according to claim 5, including the step of making a permanent appliance, and maintaining the appliance in position on the one mandible during periods of repose to maintain said mandibles in said adjusted position to ameliorate sleep apnea.

7. A method of treating a patient having a malocclusion between the upper and lower mandibles according to claim 5, including subsequently proceeding with prosthodontics while the mandibles are in said optimal line occlusal contact.

8. A method of treating a patient having a malocclusion between the upper and lower mandibles according to claim 5, including subsequently proceeding with Implantology while the mandibles are in said optimal line occlusal contact.

* * * * *